(12) United States Patent
Mani et al.

(10) Patent No.: US 8,936,603 B2
(45) Date of Patent: Jan. 20, 2015

(54) PNEUMATIC SURGICAL INSTRUMENT AND CORRESPONDING METHODS FOR PENETRATING, RESECTING AND MICROFRACTURING BONE

(76) Inventors: Frederic Mani, Dully (CH); Thierry Monnier, Les Rousses (FR); Alain Lebet, Lausanne (CH); Kareem Boulos, Chexbres (CH)

( * ) Notice: Subject to any disclaimer, the term of this patent is extended or adjusted under 35 U.S.C. 154(b) by 213 days.

(21) Appl. No.: 13/413,455

(22) Filed: Mar. 6, 2012

(65) Prior Publication Data

US 2012/0232556 A1 Sep. 13, 2012

Related U.S. Application Data

(60) Provisional application No. 61/449,934, filed on Mar. 7, 2011, provisional application No. 61/449,942, filed on Mar. 7, 2011, provisional application No. 61/449,948, filed on Mar. 7, 2011, provisional application No. 61/449,958, filed on Mar. 7, 2011, provisional application No. 61/596,193, filed on Feb. 7, 2012.

(51) Int. Cl.
*A61B 17/58* (2006.01)
*A61B 17/60* (2006.01)
*A61F 2/00* (2006.01)
*A61B 17/00* (2006.01)
*A61B 17/16* (2006.01)
(Continued)

(52) U.S. Cl.
CPC ............ *A61B 17/1604* (2013.01); *A61B 17/92* (2013.01); *A61F 2/4609* (2013.01); *A61F 2/4612* (2013.01); *A61F 2/4637* (2013.01); *A61B 2017/00544* (2013.01); *A61B 2017/00548* (2013.01); *A61B 2017/922* (2013.01); *A61B 2017/924* (2013.01); *A61F 2/34* (2013.01); *A61F 2/3609* (2013.01); *A61F 2002/4619* (2013.01); *A61F 2002/4681* (2013.01); *A61F 2002/4694* (2013.01)
USPC .......................................... 606/100; 606/190

(58) Field of Classification Search
CPC .............................. A61B 17/92; A61F 2/4637
USPC ................... 606/171, 184, 185, 190, 99, 100; 433/118, 150; 173/221
See application file for complete search history.

(56) References Cited

U.S. PATENT DOCUMENTS

| 2,275,102 A | 3/1942 | Fitzsimmons |
| 3,250,334 A | 5/1966 | Sussman |

(Continued)

FOREIGN PATENT DOCUMENTS

| EP | 0317507 | 4/1992 |
| EP | 1163882 | 9/2003 |

(Continued)

*Primary Examiner* — David Bates (57) ABSTRACT

Various embodiments of components, devices, systems and methods are provided for a pneumatic surgical instrument having a distal end of a probe configured to penetrate bone, resect or microfracture bone. The injury caused to the bone by the penetration, resection or microfracturing of same causes blood to flow to the injury site and promote the growth of new bone at the site. Holes or recesses in the bone may also be employed to treat arthritis in patient, to form holes or recesses in which one or more orthopedic implants are attached or anchored to same, form microfractures in bone, resect bone, perform osteotomies, or to carry out yet other surgical procedures in bone.

21 Claims, 10 Drawing Sheets

(51) Int. Cl.
   *A61B 17/92* (2006.01)
   *A61F 2/46* (2006.01)
   *A61F 2/34* (2006.01)
   *A61F 2/36* (2006.01)

(56) References Cited

U.S. PATENT DOCUMENTS

| | | | |
|---|---|---|---|
| 4,016,873 A | 4/1977 | Anderson | |
| 4,131,165 A | 12/1978 | Wanner et al. | |
| 4,150,656 A * | 4/1979 | Curran | 124/74 |
| 4,298,074 A * | 11/1981 | Mattchen | 173/129 |
| 4,357,940 A * | 11/1982 | Muller | 606/190 |
| 4,399,813 A * | 8/1983 | Barber | 606/99 |
| 4,462,395 A | 7/1984 | Johnson | |
| 4,476,861 A | 10/1984 | Dimakos | |
| 4,716,890 A | 1/1988 | Bichel | |
| 5,057,112 A | 10/1991 | Sherman | |
| 5,108,400 A | 4/1992 | Appel et al. | |
| 5,160,336 A | 11/1992 | Favre | |
| 5,171,313 A | 12/1992 | Salyor | |
| 5,352,230 A * | 10/1994 | Hood | 606/99 |
| D362,503 S | 9/1995 | Cook et al. | |
| 5,449,363 A | 9/1995 | Vrust et al. | |
| 5,613,483 A | 3/1997 | Lukas et al. | |
| 5,626,584 A | 5/1997 | Young | |
| 5,906,623 A | 5/1999 | Peterson | |
| 5,980,528 A | 11/1999 | Salys | |
| 6,152,930 A | 11/2000 | Mastrorio et al. | |
| 6,264,660 B1 * | 7/2001 | Schmidt et al. | 606/100 |
| 7,048,073 B2 | 5/2006 | Hezeltine | |
| 7,326,217 B2 | 2/2008 | Bubb | |
| 7,407,070 B2 | 8/2008 | Hezeltine | |
| 7,470,274 B2 | 12/2008 | Lebet | |
| 7,485,149 B1 | 2/2009 | White | |
| 7,569,057 B2 | 8/2009 | Liu et al. | |
| 7,604,637 B2 | 10/2009 | Johnson et al. | |
| 7,811,256 B2 | 10/2010 | Landman et al. | |
| 2002/0010486 A1 | 1/2002 | Hirt | |
| 2003/0000774 A1 | 1/2003 | Highley | |
| 2004/0073223 A1 * | 4/2004 | Burkinshaw | 606/79 |
| 2006/0069395 A1 | 3/2006 | Lebet | |
| 2006/0100553 A1 | 5/2006 | Lodin | |
| 2009/0118741 A1 | 5/2009 | Lebet | |
| 2010/0305624 A1 * | 12/2010 | Lozier et al. | 606/86 R |
| 2012/0022545 A1 | 1/2012 | Lebet | |

FOREIGN PATENT DOCUMENTS

| | | |
|---|---|---|
| WO | WO 95/22934 | 8/1995 |
| WO | WO 98/26705 | 6/1998 |

* cited by examiner

FIG. 3(a)
RISE-TIME AND FORCE OF THE ORTHOSHOCK™ vs THE HAMMER

FIG. 3(b)
RISE-TIME AND FORCE OF THE ORTHOSHOCK™ vs THE HAMMER

FIG. 4

PNEUMATIC SURGICAL INSTRUMENT AND CORRESPONDING METHODS FOR PENETRATING, RESECTING AND MICROFRACTURING BONE

RELATED APPLICATIONS

This application claims priority and other benefits from each of: (1) U.S. Provisional Patent Application Ser. No. 61/449,934 entitled "Pneumatic Instrument for Artificial Bone Markers and Therapy" to Mani et al. filed Mar. 7, 2011; (2) U.S. Provisional Patent Application Ser. No. 61/449,942 entitled "Pneumatic Instrument Bone Resection, Anchor Fixation, Arthroscopy, Osteotomy, Generating Microfractures" to Mani et al. filed Mar. 7, 2011; (3) U.S. Provisional Patent Application Ser. No. 61/449,948 entitled "Pneumatic Instrument of Hip and Ball Joint and Bone Cement" to Mani et al. filed Mar. 7, 2011; (4) U.S. Provisional Patent Application Ser. No. 61/449,958 entitled "Pneumatic Instrument for Bone Revision and Implant Removal" to Mani et al. filed Mar. 7, 2011, and (5) U.S. Provisional Patent Application Ser. No. 61/596,193 entitled "Pneumatic Surgical Instrument Configured to Deliver Shock Wave Having Fast Rise Time and Increased Energy" to Mani et al. filed Feb. 7, 2012. Each of the foregoing provisional patent applications is hereby incorporated herein, each in its respective entirety. U.S. patent application Ser. No. 13/413,551 entitled "Pneumatic Surgical Instrument and Corresponding Methods for Implanting, Extracting and Reorienting Orthopedic Implants" to Mani et al. filed on even date herewith is also hereby incorporated by reference herein in its entirety.

FIELD OF THE INVENTION

Various embodiments of the invention described herein relate to the field of surgical instrumentation, and more particularly to components, devices, systems and methods associated with a pneumatic surgical instrument configured to, penetrate, resect or microfracture bone.

BACKGROUND

Various problems can occur when forming holes or recesses in the bone of a patient, or when resecting or microfracturing bone. When engaging in such surgical procedures, physicians sometimes employ drills, chisels or other mechanical devices to form such holes or recesses, or to resect or microfracture the bone. For example, a surgical drill may be employed to form a hole or recess, which requires careful application of force to the bone by the operating physician, with uncertain results owing to non-homogeneity of the bone and other factors such as chisel, punch or drill bit placement, chisel, punch or drill bit angle, the speed of the drill, drill bit type and other variables. Such mechanical devices and other surgical tools can provide equally unreliable and inconsistent results.

What is needed is a surgical instrument that eases the formation of holes or recesses in bone, or the resecting or microfracturing of same, that is highly repeatable, consistent and predictable in the application of force and energy.

SUMMARY

In one embodiment, there is provided a pneumatic surgical instrument configured to penetrate, resect or microfracture bone comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, wherein the probe has a distal end configured and shaped to penetrate, resect or microfracture bone, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe, the shockwave delivered by the probe to the bone being substantially repeatable by the instrument when the trigger is actuated again by the user.

In another embodiment, there is provided a method of penetrating, resecting or microfracturing bone with a pneumatic surgical instrument configured to generate and deliver a shockwave to a probe disposed at the distal end of the instrument, the surgical instrument comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, wherein the probe has a distal end configured and shaped to penetrate resect or microfracture bone, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe, the shockwave delivered by the probe to the bone being substantially repeatable by the instrument when the trigger is actuated again by the user, the method comprising positioning the distal end of the probe or the impactor in contact with a patient skin or bone at a location where a recess or hole in the bone is desired to be formed, or where the bone is to be resected or microfractured, and actuating the trigger mechanism to deliver the shockwave to the probe and thence to the distal end of the probe thereby to penetrate, resect or microfracture the bone.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

The drawings are not necessarily to scale. Like numbers refer to like parts or steps throughout the drawings.

DETAILED DESCRIPTIONS OF SOME EMBODIMENTS

Figure 1A:
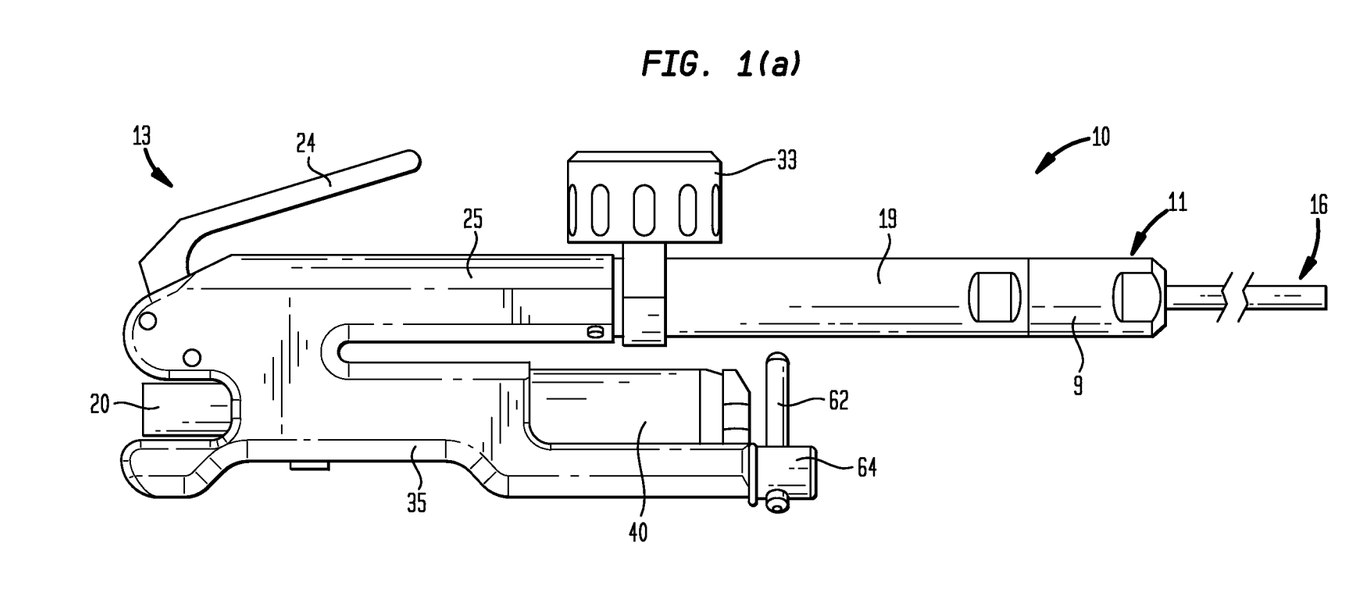
FIG. 1(a) shows a side view according to one embodiment of pneumatic surgical instrument 10.
Figure 1B:
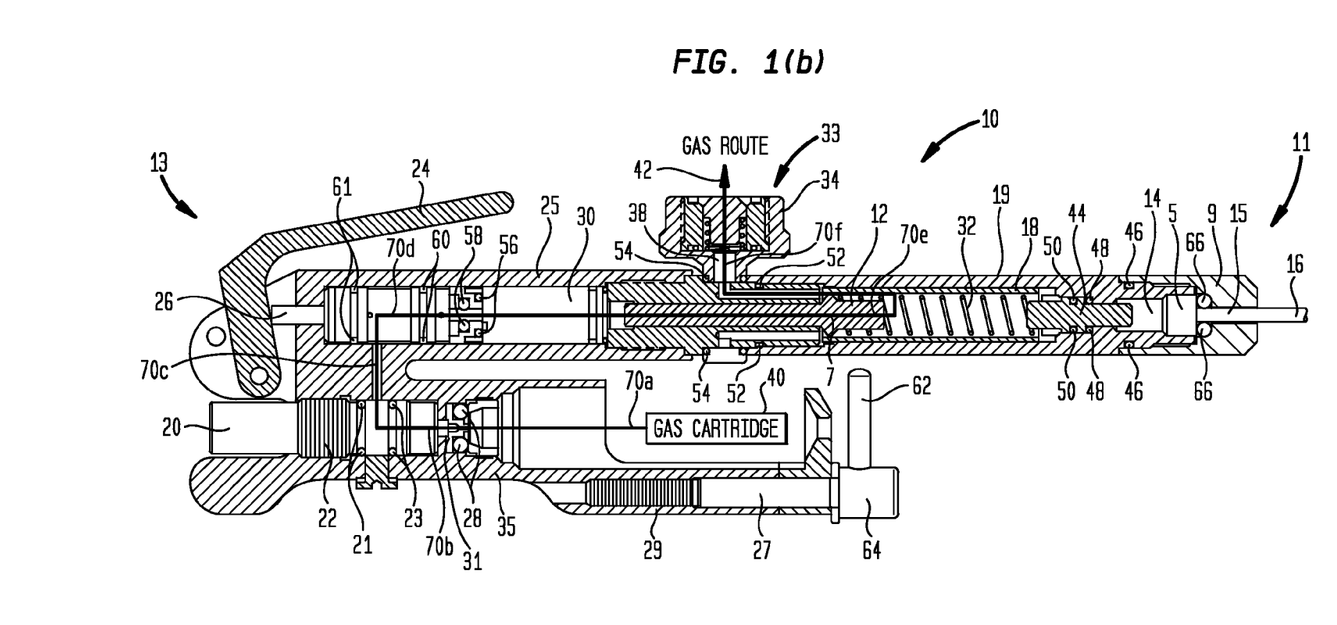
FIG. 1(b) shows a cross-sectional view according to one embodiment of pneumatic surgical instrument 10.
Figure 1C:
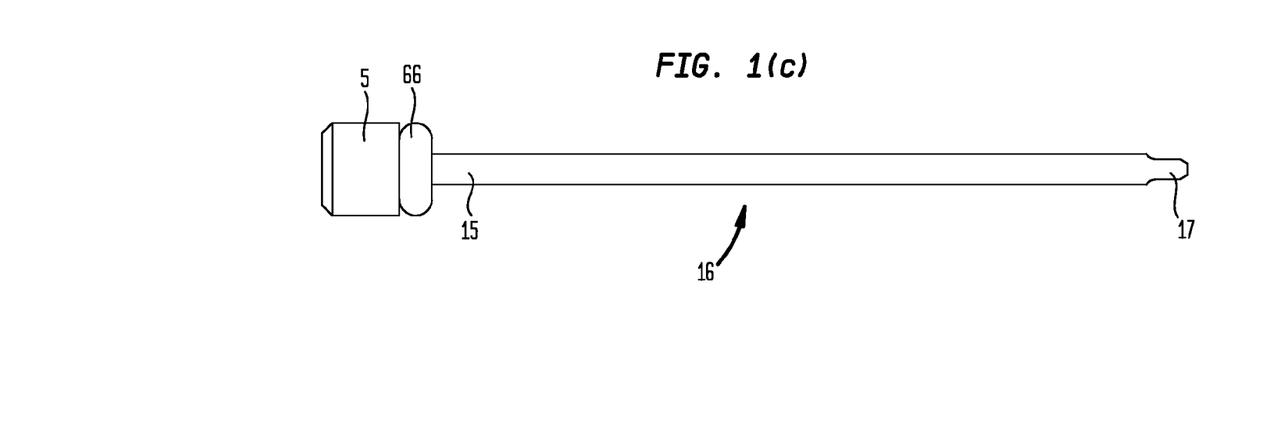
FIG. 1(c) shows a side view according to one embodiment of probe 16.
Figure 1D:
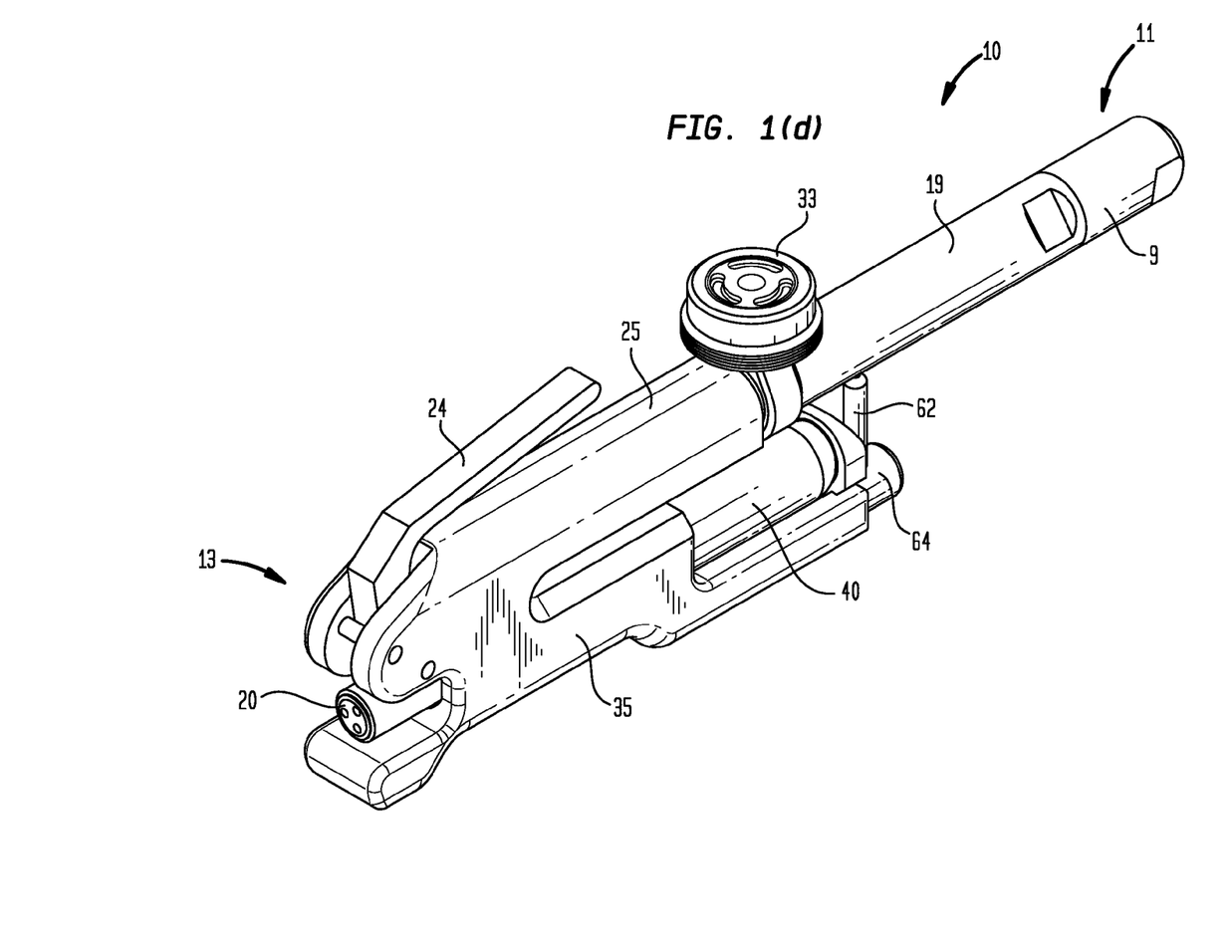
FIG. 1(d) shows a top rear perspective view according to one embodiment of pneumatic surgical instrument 10.

Referring now to FIGS. 1(a), 1(b) and 1(d), there are shown side, cross-sectional and top rear perspective views according to one embodiment of pneumatic surgical instrument 10, a commercial embodiment of which is known by the name OrthoShock™ and manufactured by OrthoWin™ of Gland, Switzerland. As shown in FIGS. 1(a), 1(b), 1(c) and 1(d), pneumatic surgical instrument 10 comprises striker 12, which in one embodiment is a piston. Removable probe or shockwave transfer device 16 is mountable on distal end 11 of instrument 10. Pressure regulator 20 is operably connectable to gas cartridge 40, which is mountable on or in instrument 10. According to one embodiment, gas cartridge 40 is a medical-grade $CO_2$ cartridge. Further according to one embodiment, trigger mechanism 30 comprises trigger or trigger handle 24, and trigger mechanism 30 is operably connected to pressure regulator 20 and striker 12. According to one embodiment, instrument 10 includes front metal housing 19, rear top metal housing 25, and rear bottom housing 35.

FIG. 1(c) shows a side view according to one embodiment of probe 16, where O-ring 66 is pre-mounted on proximal end 15 of the shaft projecting towards distal end 17 from a distal surface of proximal probe terminus 5. According to various embodiments, and as discussed in further detail below, the thickness, mechanical properties or materials, stiffness, or other properties of O-ring 66 may be selected to provide a desired amount of displacement or other desired performance characteristics when surgical instrument 10 is triggered or actuated. In addition, instrument 10 may be configured to receive more than one O-ring 66 between proximal terminus 5 and probe cap 9.

Figure 2A:
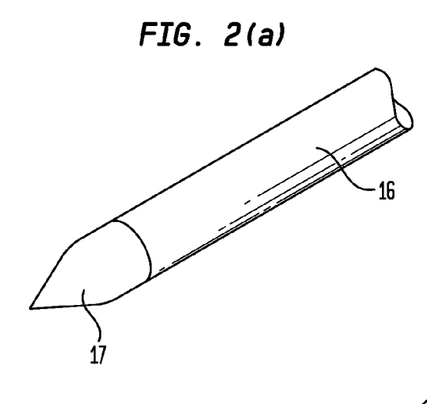
FIGS. 2(a) through 2(h) show various embodiments of distal end 17 of probe 16.
Figure 2B:
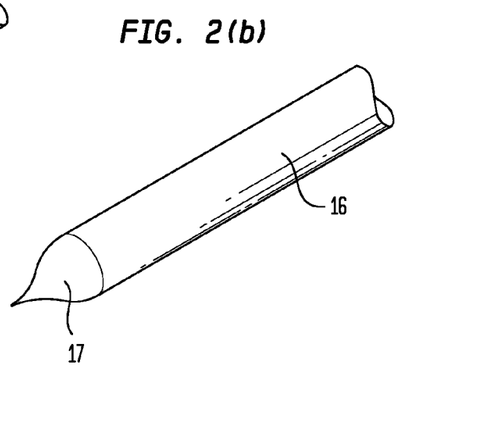
Figure 2C:
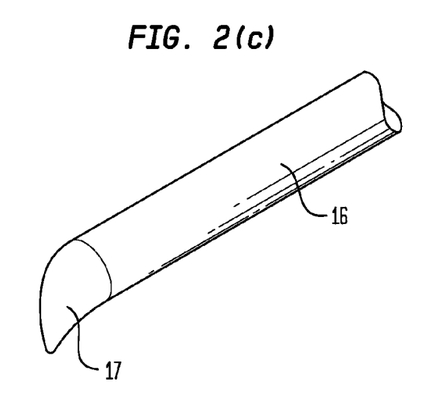
Figure 2D:
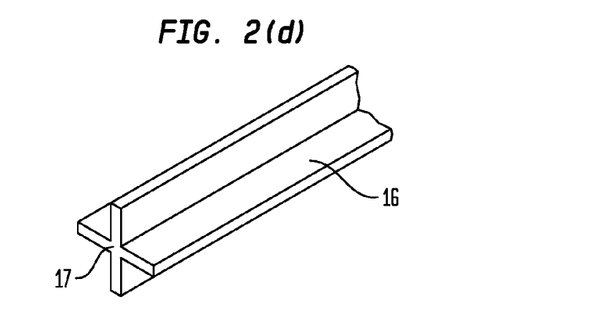
Figure 2E:
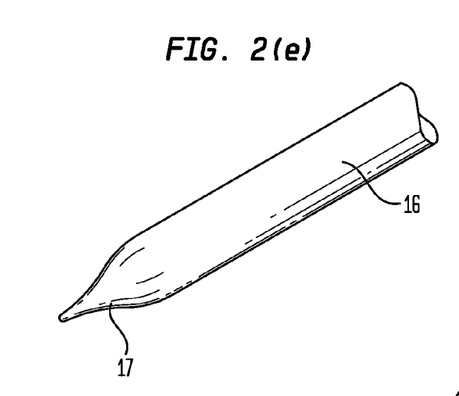
Figure 2F:
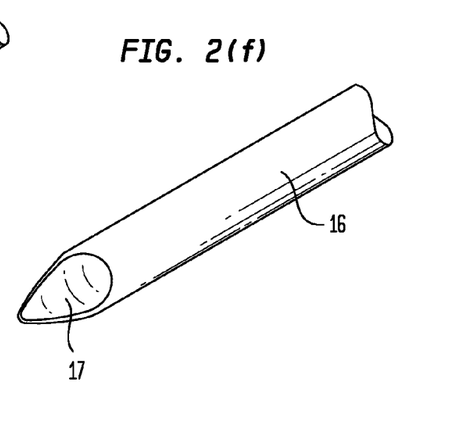
Figure 2G:
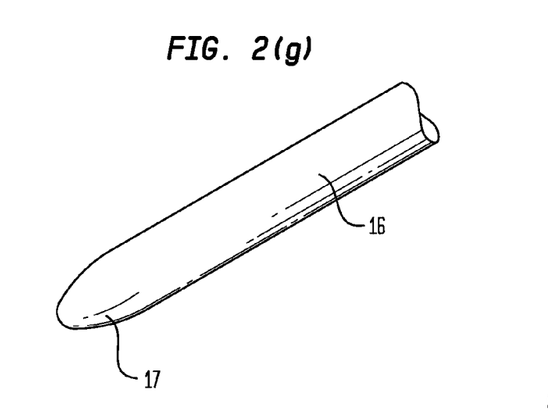
Figure 2H:
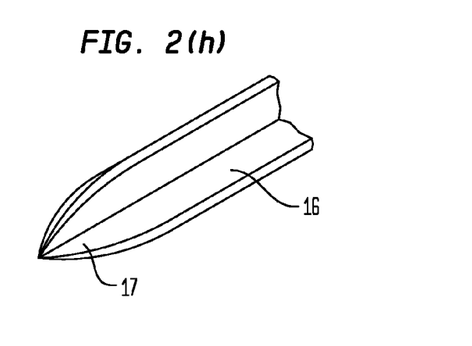

Continuing to refer to FIGS. 1(a) through 1(d), probe 12 has distal end 17 configured and shaped to engage: (a) at least a portion of a surface of an orthopedic implant 82, 84, 88, 90, 122, 124, or 126 (see, for example, FIG. 2(c) herein), (b) a device such as a punch configured to be placed between the orthopedic implant and the distal end of the probe (not shown in the Figures), or (c) an orthopedic implant impactor 80 configured to receive distal end 17 of probe 16 therein or thereon (see, for example, FIGS. 3(a) through 5(b) herein).

According to some embodiments, impactor 80 is configured and shaped to engage at least a portion of the surface of an orthopedic implant. Instrument 10 is configured to deliver at least one shock wave to probe 16 when trigger 24 is actuated by a user and a predetermined volume of gas stored at a predetermined range of pressures in instrument 10 is released thereby to cause striker 12 to move towards distal end 11 of instrument 10 and deliver the shock wave to proximal end 15 of probe 16.

The shockwave delivered by instrument 10 and probe 16 is substantially repeatable by instrument 10 when trigger 24 is actuated again by the user for the delivery of a subsequent shockwave by instrument 10 after the volume of gas exhausted by instrument 10 through gas exhaust device 33 has been replenished within instrument 10 from gas cartridge 40 through gas regulator 20.

According to one embodiment, the predetermined volume of gas stored at a predetermined range of pressures is contained in a chamber disposed within trigger mechanism 30, and is released to force the striker towards distal end 11 of instrument 10 when trigger mechanism 30 is actuated by the user by means of trigger handle 24 and actuator 26. Other means of triggering trigger mechanism 30 are contemplated, such as solenoids, mechanically depressible buttons, and so on. Moreover, the chamber containing the predetermined volume of gas stored at a predetermined range of pressures in instrument 10 may be housed elsewhere in instrument 10 other than as part of trigger mechanism 30, such as, by way of example, in a chamber disposed in or attached to pressure regulator 20, or in another location within or on instrument 10. Note that in the embodiment of instrument 10 shown in FIGS. 1(a), 1(b) and 1(c), striker 12 is disposed within longitudinal striker sleeve 18, although other embodiments are contemplated.

Further according to various embodiments, pneumatic instrument 10 may be configured such that the shockwave provided by probe 16 has a rise time ranging between about 2 microseconds and about 20 microseconds, between about 4 microseconds and about 16 microseconds, or between about 6 microseconds and about 10 microseconds, more about which is said below.

Referring still to FIGS. 1(a) through 1(d), and according to one embodiment, instrument 10 comprises removable probe cap 9, which is configured to receive proximal end 15 of probe 16 therein or therethrough, where probe cap 9 is mountable on distal end 11 of instrument 10, and where proximal probe terminus 5 is located proximally within instrument 10 behind probe cap 9. Firing pin 44 is disposed between a distal end of striker 12 and a proximal end of firing pin receiver 14. The distal end of striker 12 is configured to engage and strike a proximal end of firing pin 44 and drive same towards firing pin receiver 14, which is configured to receive the distal end of firing pin 44 therein and transfer the shockwave delivered thereby to proximal probe terminus 5.

As further shown in FIG. 1(c), probe O-ring 66 is disposed near proximal end 15 of probe 16 between an inner surface of probe cap 9 and a distal portion of probe terminus 5. In one embodiment, probe O-ring 66 comprises nitrile and has a thickness ranging between about 2 mm and about 3 mm, although other ranges of the thickness of O-ring 66 are contemplated, such as between about 1 mm and about 6 mm, between about 1.5 mm and about 5 mm, between about 2 mm and about 4 mm. In one embodiment, O-ring 66 has an inner diameter of about 2.8 mm, an outer diameter of about 7 mm, and a thickness of 2.64 mm. Other diameters and thicknesses of O-ring 66 are contemplated, however. According to one embodiment, probe 16 is displaced by about 0.5 mm when instrument 10 is actuated. Other amounts of the displacement of probe 16 when instrument 10 is triggered or actuated may be provided, however, such as displacement of about 0.2 mm, about 0.4 mm, about 0.6 mm, about 0.8 mm, and about 1 mm.

In conjunction with the amount of force provided by the distal end of striker 12 to firing pin 44, firing pin receiver 14, and probe terminus 5, the number, thickness or other properties of O-rings 66 may be configured to provide a desired amount of displacement of probe 16, or a desired force or energy signature, when instrument 10 is triggered. Further according to some embodiments, other O-rings 46, 48, 50, 52, 54, 56, 58, 60, 61, 21, 23 and 28 in instrument 10 may also comprise nitrile, which does not absorb $CO_2$ gas and thus prevents the degradation or expansion of such O-rings caused by exposure to $CO_2$ gas.

Still referring to FIG. 1(b), and according to one embodiment, pressure regulator 20 includes a pin 31 that is configured to puncture gas cartridge 40 when replaceable gas cartridge 40 is mounted in or on instrument 10. Gas cartridge 40 may be inserted or removed form instrument 10 by turning gas cartridge replacement and removal mechanism handle 62, and corresponding shaft end 64, rod 27, and threaded portion 29 inwardly or outwardly, as the case may be. Pressure regulator 20 directs and regulates the pressure of gas originating in cartridge 40 to trigger mechanism 30, and includes spring 22, which is configured to push a valve located in pressure regulator 20 closed after a predetermined amount or volume of gas has been emitted from cartridge 40 into pressure regulator 20 and trigger mechanism 30. According to some embodiments, gas regulator 20 is configured to provide pressurized gas to trigger mechanism 30 at pressures ranging between about 15 bars and about 60 bars, or between about 25 bars and about 35 bars. A nominal regulated pressure of 29 bars is preferred according to one embodiment.

Continuing to refer to FIG. 1(b), there are shown interconnected gas passageways 70a, 70b, 70c, 70d, 70e, and 70f, which are routed, respectively, through gas cartridge 40, gas regulator 20, between gas regulator 20 and trigger mechanism 30, trigger mechanism 30, striker 12 (through central aperture 7), and around the top portion of striker 12. Gas travelling through such passageways is ultimately exhausted through gas exhaust device 33 as exhaust gas 42. According to one embodiment, and as shown in FIG. 1(b), gas exhaust device 33 comprises gas exhaust filter housing 34, a replaceable gas exhaust filter cartridge (not shown in the drawings), and gas exhaust filter valve 38. Gas exhaust device 33 is configured to trap particulate contaminants in the replaceable gas exhaust filter cartridge that may be present in gas provided by gas cartridge 40, and prevent contamination of the sterile field during a surgical procedure.

Referring to FIGS. 1(a) through 1(d), and according to one embodiment, probe 16 comprises a metal or metal alloy such as stainless steel, and has a length ranging between about 10 cm and about 30 cm, and a diameter ranging between about 2.8 mm and about 3.4 mm. Other probe lengths and diameters are also contemplated, however.

Figure 1E:
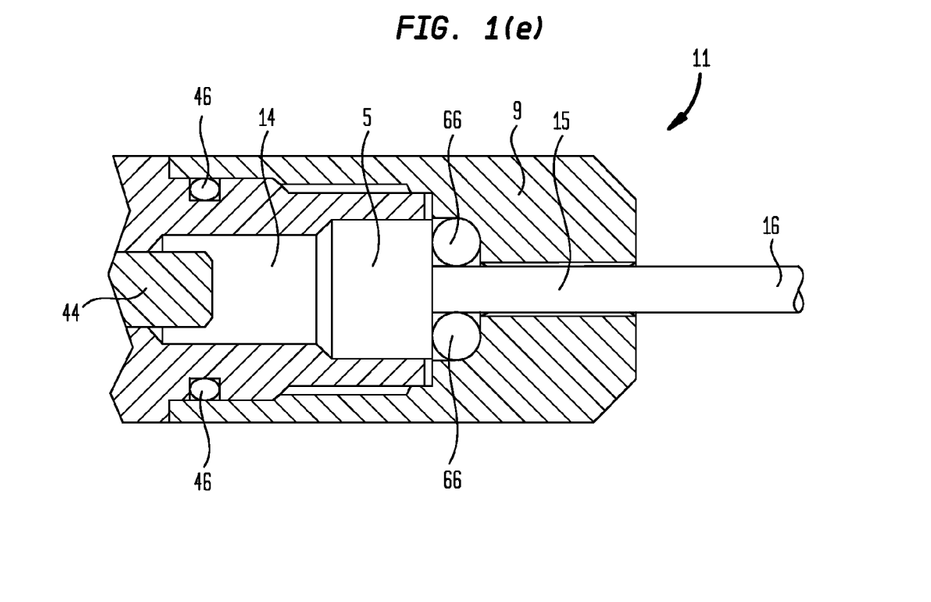
FIG. 1(e) through FIG. 1(g) show various embodiments of distal end 11 of instrument 10 and probe cap 9, proximal probe terminus 5, and O-ring(s) 66.
Figure 1F:
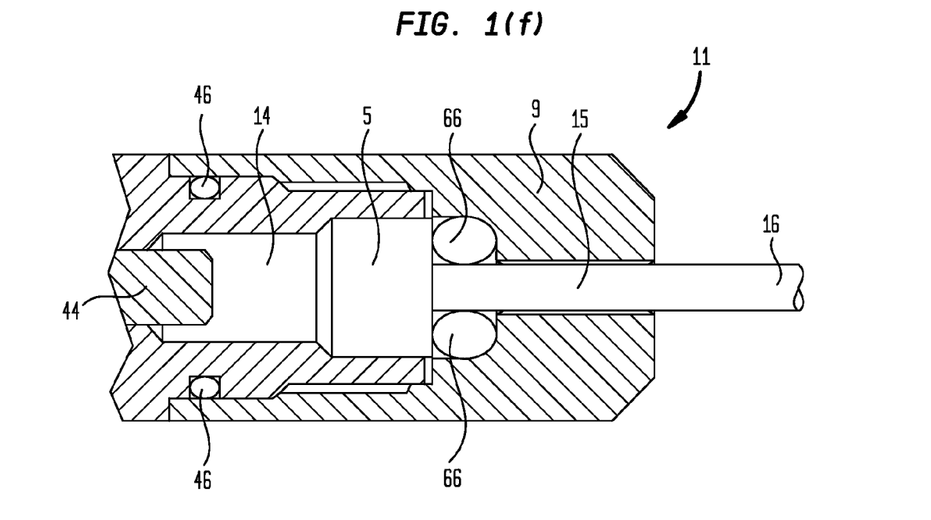

FIGS. 1(e) through 1(f) illustrate various embodiments of certain details concerning distal end 11 of instrument 10, and more particularly how the configurations and dimensions thereof may be adjusted or modified to provide different functional performance characteristics of instrument 10 in use.

FIG. 1(e) shows an enlarged cross-sectional view of distal end 11 of instrument 10 that conforms with that shown in FIG. 1(b) hereof. As shown in FIG. 1(e), a single O-ring 66 is disposed between a distal forward-facing surface of proximal probe terminus 5 and an internal surface of probe cap 9. When instrument 10 is triggered or actuated, firing pin 44 is stricken by striker 12 (not shown in FIG. 1(e)), which then pushes firing pin receiver 14 forwardly in a distal direction against a proximal surface of probe terminus 5, the distal surface of which is then pushed against O-ring 66 confined against a distal internal surface of probe cap 9, thereby to cause displacement of probe 16 in the distal direction. In the embodiment shown in FIG. 1(e), probe 16 is displaced about 0.5 mm in the distal direction when the pressure at which instrument 10 operates is about 29 bars, and when O-ring 66 has an inner diameter of about 2.8 mm, an outer diameter of about 7 mm, and a thickness of 2.64 mm as described above.

In FIG. 1(f), a single O-ring 66 is also disposed between a distal forward-facing surface of proximal probe terminus 5 and an internal surface of probe cap 9, but O-ring 66 of FIG. 1(f) is thicker than that of FIG. 1(e), and the space occupied by O-ring 66 in FIG. 1(f) is larger and wider than that of FIG. 1(e). Probe cap 9 of FIG. 1(f) is thus configured differently from that of FIG. 1(e) so as to accommodate a larger O-ring 66, and according to the physical properties of O-ring 66 that has been selected for use may result in increased displacement of probe 16 than the embodiment shown in FIG. 1(e) when instrument 10 is triggered or actuated, or may result in other changes in other functional performance characteristics of instrument 10 in use, as discussed above.

Figure 1G:
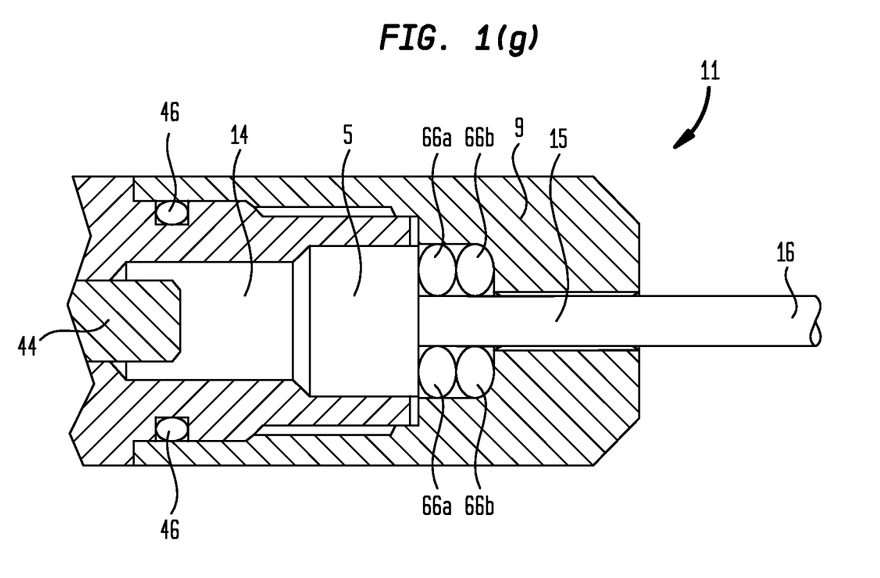

In FIG. 1(g), two O-rings 66a and 66b are disposed between a distal forward-facing surface of proximal probe terminus 5 and an internal surface of probe cap 9, and the space occupied by O-rings 66a and 66b in FIG. 1(g) is also larger and wider than that of FIG. 1(e). Probe cap 9 of FIG. 1(f) is thus configured differently from that of FIG. 1(e) so as to accommodate two O-rings 66a and 66b, and according to the physical properties of O-rings 66a and 66b that have been selected for use may result in increased displacement of probe 16 than the embodiment shown in FIG. 1(e) when instrument 10 is triggered or actuated, or may result in other changes in other functional performance characteristics of instrument 10 in use, as discussed above.

As shown in FIGS. 2(a) through 2(h), various embodiments of distal end 17 of probe 16 may be configured to penetrate, resect or microfracture bone through the successive and sequential applications of shockwaves thereto by probe 16 and distal end 17 thereof to bone. In the embodiment shown in FIG. 2(a), distal end 17 of probe 16 is pointed. In the embodiment shown in FIG. 2(b), distal end 17 of probe 16 features harpoon-shaped protrusions. In the embodiment shown in FIG. 2(c), distal end 17 of probe 16 is pointed and deflected away from a longitudinal axis associated with probe 16. In the embodiment shown in FIG. 2(d), distal end 17 of probe 16 is cross-shaped. In the embodiment shown in FIG. 2(e), distal end 17 of probe 16 forms a tapered sharp point. In the embodiment shown in FIG. 2(f), distal end 17 of probe 16 is U-shaped. In the embodiment shown in FIG. 2(g), distal end 17 of probe 16 forms a blunted and rounded tip. In the embodiment shown in FIG. 2(h), distal end 17 of probe 16 forms a tapered cross-shape. Other configurations of distal tip 16 are contemplated. Such as serrated tips, blade-shaped tips, and so on, that have shapes or configurations suitable for penetrating, resecting or microfracturing bone.

In conjunction with the selection of O-ring 66 having a desired thickness, stiffness, material or other characteristics, and the selection of an removable probe cap 9 having a suitable configuration and interior volume for housing O-ring(s) 66, instrument 10 may be configured to provide customizable amounts of displacement or other functional performance characteristics of probe 16 when instrument 10 is actuated or triggered. That is, one or more of O-ring(s) 66 and removable probe cap 9 having certain predetermined characteristics may be selected to provide customizable amounts of displacement or other performance characteristics of probe 16. According to one embodiment, probe 16 is displaced by about 0.5 mm when instrument 10 is actuated, although other displacements of probe 16 may be provided by instrument 10, such as about 0.2 mm, about 0.4 mm, about 0.6 mm, about 0.8 mm, about 1 mm, and about 1 mm. Other displacements are also contemplated.

Figure 3A:
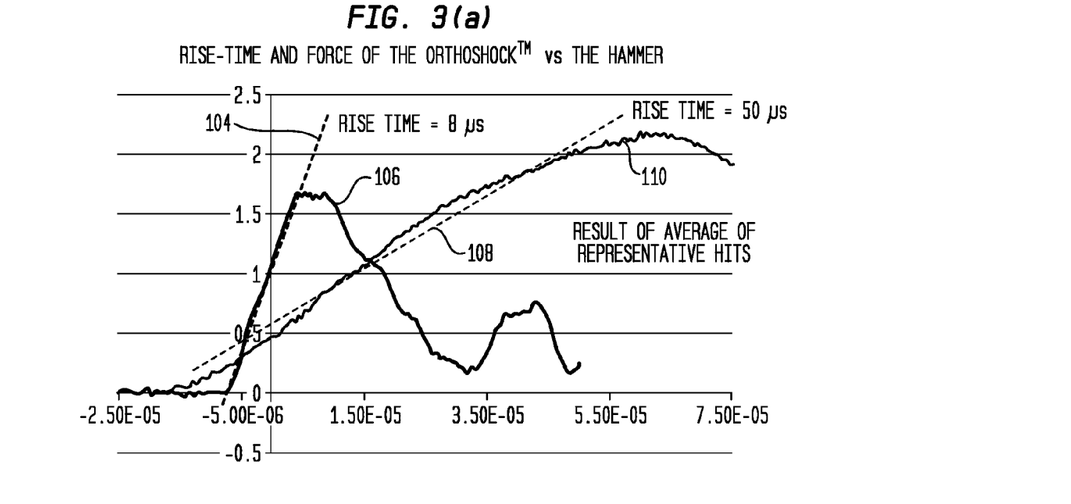
FIGS. 3(a) and 3(b) show various characteristics of the rise times and forces of the shock waves generated by instrument 10.
Figure 3B:
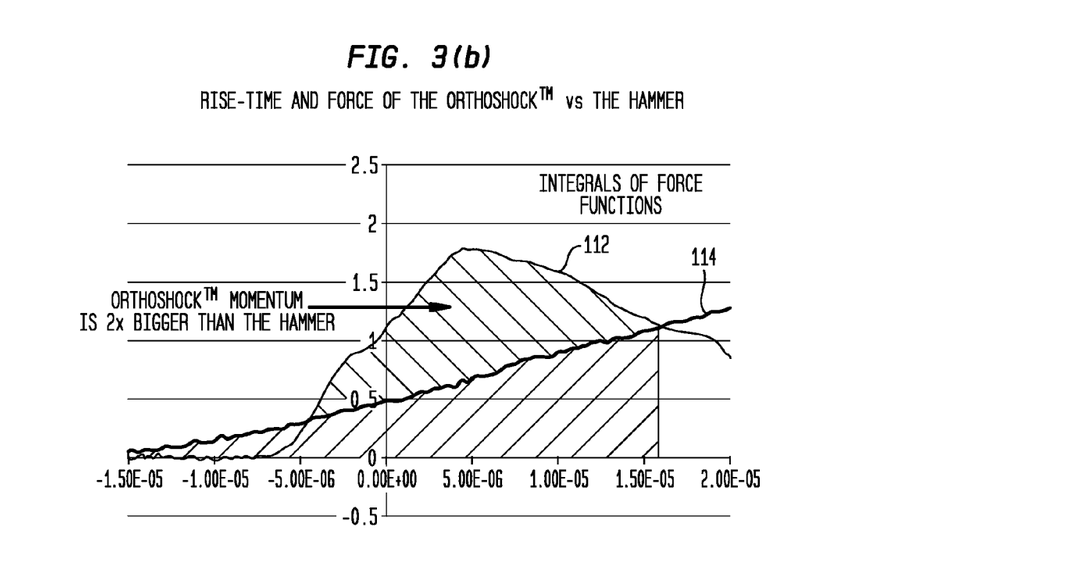

Referring now to FIGS. 3(a) and 3(b), there are shown various characteristics of the rise times and forces of the shock waves generated by a commercial embodiment of instrument 10 of FIGS. 1(a) through 1(c) known as the OrthoShock™ surgical instrument. As illustrated in FIG. 3(a), there is shown the output signal (or shockwave or impulse force) delivered according to one embodiment of the OrthoShock surgical instrument disclosed and described herein. The shockwave or impulse force output signal delivered by an OrthoShock™ surgical instrument to an orthopedic implant or device is juxtaposed with the output signals provided by a conventional orthopedic hammer. As will be seen by referring to FIG. 3(a), the rise time, or the amount of time over which the shockwave or impulse force is provided by instrument 10 is much shorter than that provided by a conventional orthopedic hammer. In the example shown in FIG. 3(a), the total rise time is about 6 microseconds, as compared to a 50 microsecond rise time characteristic of a hammer employed for the same purpose. The steeper the curve of the output signal, the better the initial impulse. Further as shown in FIG. 3(a), the rise time of the OrthoShock™ surgical instrument is about five times greater than that of a corresponding orthopedic hammer.

FIG. 3(b) shows a comparison of integrated output shockwave or impulse force output signals provided by one embodiment of the surgical instrument described and disclosed herein relative to those provided by a hammer, and corresponds to the results shown in FIG. 3(a). The greater the integral, especially during the first 20 microseconds in the context of delivering shockwave to an artificial hip implant insert for the purpose of ejecting same, the bigger the change in momentum, and the more energy that is usefully transferred to the orthopedic implant or device to cause its ejection from an artificial hip socket. This means that use of surgical instrument 10 disclosed and described herein results in particularly efficacious and easy removal, reorientation or insertion of an artificial hip implant insert with respect to an artificial hip implant socket.

Figure 4:
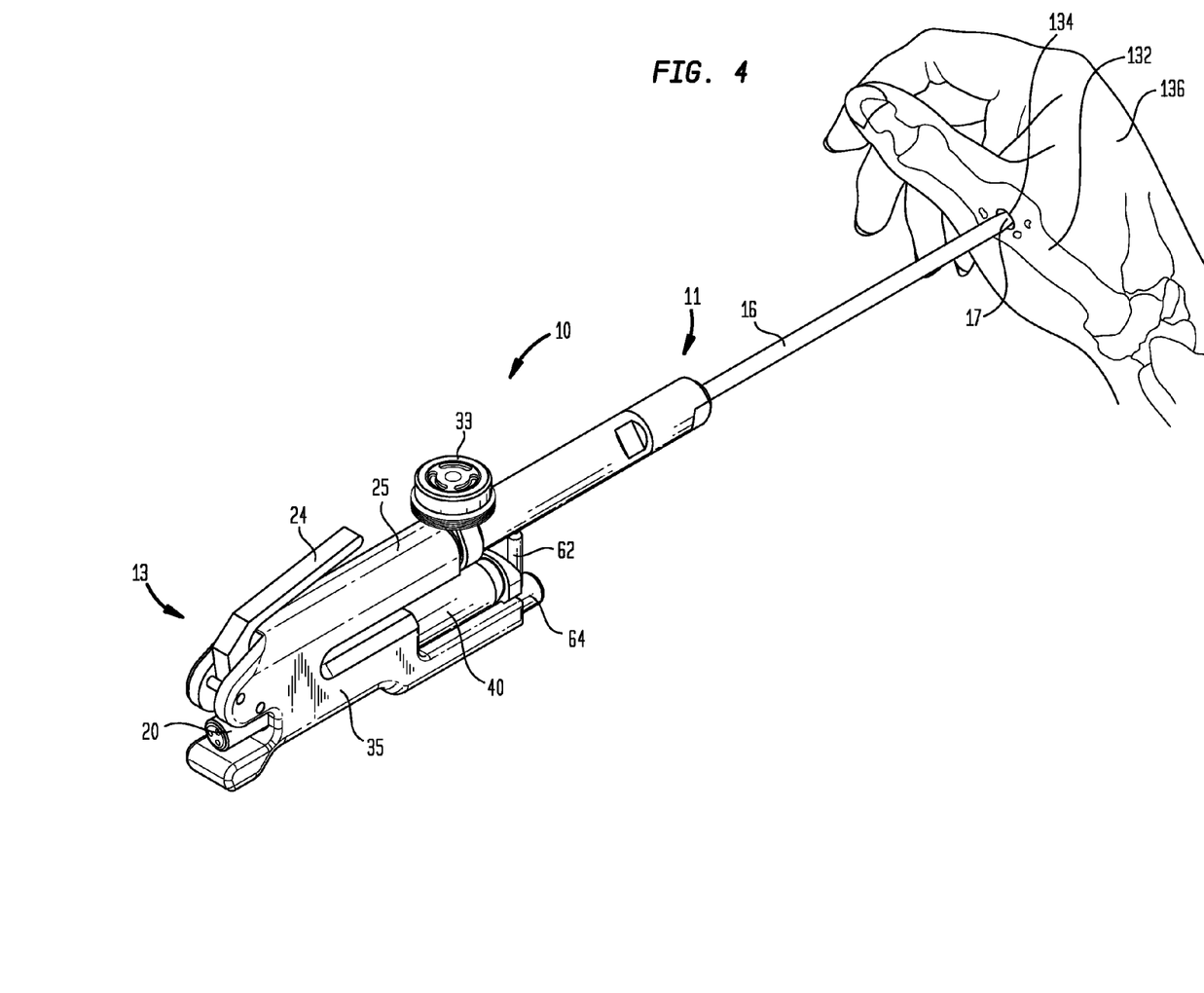
FIG. 4 shows one embodiment of instrument 10 having distal end 17 of probe 16 positioned on a hand 136 of patient for the purpose of effecting arthrodesis.

Referring now to FIG. 4, there is shown one embodiment of instrument 10 having distal end 17 of probe 16 positioned on a joint 132 of a patient's hand 136 to form holes or recesses 134 in joint 132 to effect arthrodesis in patient's joint 132. Instrument 10 is actuated successively and sequentially until distal end 17 of probe 16 has attained a desired depth, shape or configuration in the bone of joint 132. In one embodiment, a single shock delivered by instrument 10 to bone may penetrate same by about 0.5 mm. It is typically desired that holes in bone for treating arthrodesis be 4 to 5 mm deep, and thus 3, 4, 5 and sometimes more strikes by distal tip 17 generated by instrument 10 may be required to attain the desired depth in joint 132. A plurality of circumferentially-located holes 134 may be formed by instrument 10 around joint 132, which causes an increased flow of blood to the various injury sites formed by holes 132, and over time the promotion of the growth of new bone therein and thearearound arthrodesis). Over time, the resulting new bone growth around and in joint 132 leads to joint 132 becoming substantially rigid and unmovable, which may decrease the pain sensed by the patient in joint 132.

Figure 5:
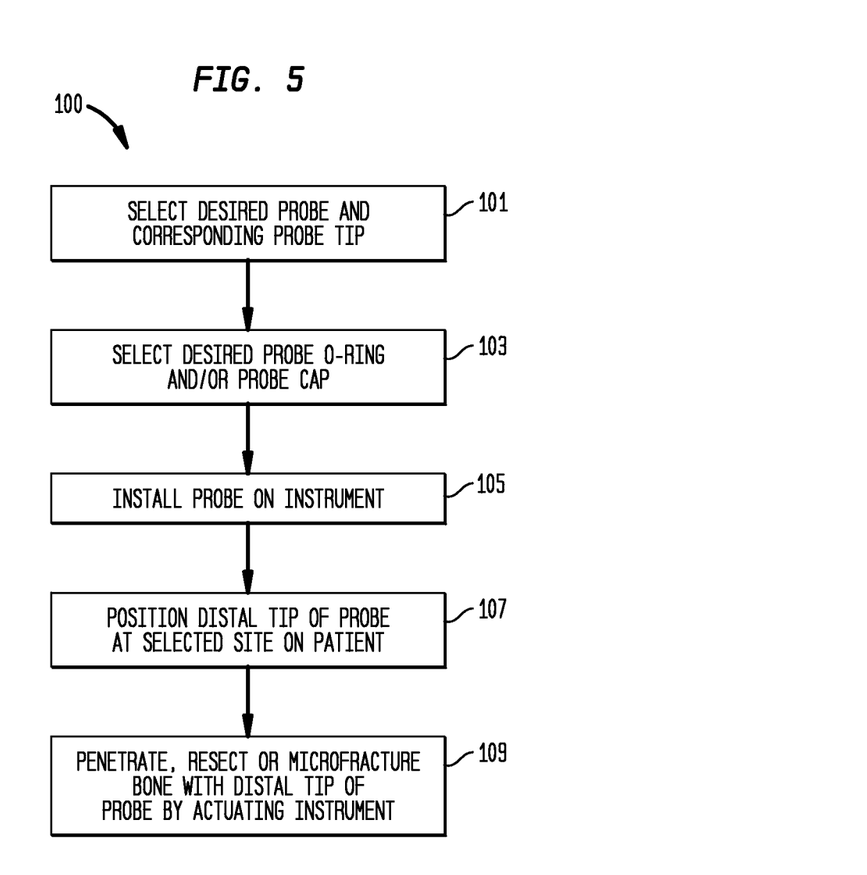
FIG. 5 shows one embodiment of a method 100 for penetrating and forming a hole or recess therein, or for resecting or microfracturing bone.

FIG. 5 shows one embodiment of a method 100 for penetrating, resecting, or microfracturing bone to form holes or recesses therein, or for resecting or microfracturing same. At step 101, probe 16 having distal end 17 of a desired shape or configuration is selected. At optional step 103, O-ring(s) 66 having desired characteristics or properties is/are selected and mounted on proximal end 15 of probe 16. Probe cap 9 and/or probe receiver 14 having desired dimensions may also be selected in step 103, followed by installing the selected probe 16 in instrument 10 and attaching probe cap 9 onto distal end 11 of instrument 10 at step 105. At step 107, distal end 17 is positioned at a selected site on the patient proximate the bone that is to be penetrated, resected or microfractured. At step 109, instrument 10 is actuated or triggered, and a shock wave is delivered to the bone by distal end 17 of probe 16, resulting in at least the beginning of the formation of a hole or recess therein, or the resection or microfracturing thereof. The process of delivering of shockwaves to bone 10 by instrument 10 continues until the hole or recess attains the desired depth and/or shape or configuration, or the desired amount of resection or microfracturing has been attained.

Other surgical procedures that may be carried out with instrument 10 described and disclosed herein include, but are not limited to, are bone resection, anchor fixation, arthroscopy, osteotomy, arthrodesis, and the generation of microfractures in bone.

The above-described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

We claim:

1. A self-contained pneumatic surgical instrument configured to penetrate, resect or microfracture bone, comprising:
   a striker;
   a removable probe mountable on a distal end of the instrument;
   at least one removable probe cap configured to receive a proximal end of the removable probe therein or therethrough, the probe cap being mountable on the distal end of the surgical instrument;
   at least one removable O-ring disposed between an inner surface of the probe cap and a distal terminus of the removable probe;
   a pressure regulator;
   a gas cartridge operably connected to the pressure regulator, the gas cartridge and pressure regulator forming portions of the self-contained pneumatic surgical instrument;
   a trigger mechanism comprising a trigger, the trigger mechanism being operably connected to the pressure regulator and to the striker;
   wherein the probe has a distal end configured and shaped to penetrate, resect or microfracture bone, the instrument is configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe, the shockwave delivered by the probe to the bone having a rise time ranging between about 2 microseconds and about 20 microseconds, the shockwave being substantially repeatable by the instrument when the trigger is actuated again by the user;
   wherein the at least one O-ring is selectable according to a thickness, mechanical properties, materials, or stiffness of the O-ring, and the at least one probe cap is selectable such that internal dimensions of the at least one probe cap are configured, thereby to provide a given amount of relative displacement between the probe and the instrument when the instrument is triggered or actuated; and
   wherein selection of a different one of the at least one O-ring and/or at least one cap provides the probe with a different relative displacement between the probe and the instrument as compared with a selection of another of the at least one cap and/or at least one O-ring.

2. The pneumatic surgical instrument of claim 1, wherein the distal end of the probe is one of pointed, cross-shaped, rounded, pointed and smooth, pointed and deflected away from a longitudinal axis associated with the probe, a tapered sharp point, U-shaped, blunted and rounded, a tapered cross-shape, serrated, and blade-shaped.

3. The pneumatic surgical instrument of claim 1, wherein the O-ring comprises nitrile.

4. The pneumatic surgical instrument of claim 1, further comprising a firing pin disposed between a distal end of the striker and the proximal end of the probe, the distal end of the striker being configured to engage and strike a proximal end of the firing pin.

5. The pneumatic surgical instrument of claim 1, wherein the probe further comprises a shaft having the probe terminus disposed at the proximal end thereof.

6. The pneumatic surgical instrument of claim 5, wherein the removable probe cap is configured to receive the shaft therethrough and to house proximally therefrom within the instrument the at least one probe O-ring disposed against a distal surface of the proximal probe terminus.

7. The pneumatic surgical instrument of claim 1, wherein the probe O-ring has a thickness ranging between about 1 mm and about 6 mm.

8. The pneumatic surgical instrument of claim 1, wherein the probe O-ring has a thickness ranging between about 2 mm and about 4 mm.

9. The pneumatic surgical instrument of claim 1, wherein the at least one removable probe cap is configured to receive a shaft of the probe therethrough and to house proximally therefrom within the instrument a plurality of probe O-rings located near a distal surface of the proximal probe terminus.

10. The pneumatic surgical instrument of claim 1, wherein the probe O-ring has a thickness ranging between about 2 mm and about 3 mm.

11. The pneumatic surgical instrument of claim 1, wherein a displacement provided by the probe when the instrument is actuated or triggered is one of about 0.2 mm, about 0.4 mm, about 0.6 mm, about 0.8 mm, about 1 mm, and about 1.2 mm.

12. The pneumatic surgical instrument of claim 1, wherein the rise time ranges between about 4 microseconds and about 16 microseconds.

13. The pneumatic surgical instrument of claim 1, wherein the rise time ranges between about 6 microseconds and about 10 microseconds.

14. The pneumatic surgical instrument of claim 1, wherein the trigger mechanism further comprises a trigger chamber configured to contain the predetermined volume of gas.

15. The pneumatic surgical instrument of claim 1, wherein the trigger mechanism further comprises a trigger handle and a trigger actuator operably couplable to the trigger handle.

16. The pneumatic surgical instrument of claim 1, wherein the pressure regulator further comprises a pin configured to puncture the gas cartridge when the gas cartridge is mounted in or on the instrument.

17. The pneumatic surgical instrument of claim 1, wherein the gas cartridge is a $CO_2$ cartridge.

18. The pneumatic surgical instrument of claim 1, wherein the gas regulator is further configured to provide pressurized gas to the trigger mechanism at pressures ranging between about 15 bars and about 60 bars.

19. The pneumatic surgical instrument of claim 1, wherein the gas regulator is further configured to provide pressurized gas to the trigger mechanism at pressures ranging between about 25 bars and about 35 bars.

20. The pneumatic surgical instrument of claim 1, wherein the probe further comprises stainless steel.

21. The pneumatic surgical instrument of claim 1, wherein the probe has a length ranging between about 10 cm and about 30 cm.

* * * * *